United States Patent [19]

Lai et al.

[11] Patent Number: 4,667,016
[45] Date of Patent: May 19, 1987

[54] ERYTHROPOIETIN PURIFICATION

[75] Inventors: Por-Hsiung Lai, Westlake Village; Thomas W. Strickland, Camarillo, both of Calif.

[73] Assignee: Kirin-Amgen, Inc., Thousand Oaks, Calif.

[21] Appl. No.: 747,119

[22] Filed: Jun. 20, 1985

[51] Int. Cl.$^4$ ............... A61K 37/24; A61K 35/22; A61K 37/36; C07K 15/14
[52] U.S. Cl. ............... 530/397; 424/95; 424/99; 424/101; 435/68; 435/172.2; 435/172.3; 435/240; 435/241; 435/948; 514/6; 530/380; 530/395; 530/399; 530/416; 530/808; 530/809; 530/834; 935/109
[58] Field of Search ............... 260/112 R, 112 B; 424/95, 99, 101; 435/68, 172.3, 172.2, 240, 241; 514/6; 530/380, 395, 397, 399, 416, 808, 809, 834; 935/109

[56] References Cited

U.S. PATENT DOCUMENTS

| | | |
|---|---|---|
| 3,033,753 | 5/1962 | White et al. ............ 424/101 |
| 3,109,774 | 11/1963 | White et al. ............ 424/101 |
| 3,111,458 | 11/1963 | White et al. ............ 424/101 |
| 4,254,095 | 3/1981 | Fisher et al. ............ 424/88 X |
| 4,289,690 | 9/1981 | Pestka et al. ............ 260/112 R |
| 4,303,650 | 12/1981 | Takezawa et al. ............ 514/21 |
| 4,465,624 | 8/1984 | Chiba et al. ............ 260/112 R |
| 4,558,005 | 12/1985 | Goldwasser et al. ....... 260/112 B X |
| 4,568,488 | 2/1986 | Lee-Huang ............ 530/397 |

OTHER PUBLICATIONS

J. Biol. Chem. 255, No. 4, 1536–1541 (1980), Takagaki et al.
Advances in Chromatography, 20, (1982), Giddings editor, p. 43.
High Performance Liquid Chromatography of Proteins & Peptides, Proceedings of the 1st International Symposium, Hearn editor, (1981), pp. 161–165, O'Hare et al.
Analytical Biochemistry, 99, 1–21 (1979), Brown et al.
Endocrinology, 114, (6), 2223–2227 (1984), Parsons et al.
Vydac TM Comprehensive Guide to Reverse Phase Materials for HPLC, Harrison et al. (1984), pp. 1–12.

Primary Examiner—Howard E. Schain
Attorney, Agent, or Firm—Marshall, O'Toole, Gerstein, Murray & Bicknell

[57] ABSTRACT

Chromatographic procedures are individually and jointly applied to the rapid and efficient isolation of biologically active proteins and especially glycoproteins such as recombinant erythropoietin present in the medium of growth of genetically transformed mammalian host cells. Illustratively, recombinant EPO is isolated from culture fluids by reverse phase chromatography employing a $C_4$ or $C_6$ column and elution with ethanol. Recombinant erythropoietin may also be purified by anion exchange chromatography employing, e.g., a DEAE resin, with preliminary selective elution of contaminant materials having a lower pKa than erythropoietin from the resin under conditions mitigating against acid activated protease degradation. Practiced serially, the two chromatographic procedures allow for high yields of biologically active recombinant erythropoietin from mammalian cell culture media.

11 Claims, No Drawings

ERYTHROPOIETIN PURIFICATION

BACKGROUND

The present invention relates generally to protein purification employing chromatographic techniques. More particularly, the present invention relates to procedures for the rapid and efficient isolation of biologically active proteins such as glycoproteins and especially glycoproteins having high sialic acid content (e.g., erythropoietic factors such as erythropoietin) from natural (e.g., blood fractions and urine) and recombinant (e.g., genetically transformed mammalian cell culture fluid) sources.

Numerous techniques have in the past been applied in preparative separations of biochemically significant materials. Commonly employed preparative separatory techniques include: ultrafiltration, column electrofocusing, flat-bed electrofocusing, gel filtration, electrophoresis, isotachophoresis and various forms of chromatography. Among the commonly employed chromatographic techniques are ion exchange chromatography and adsorption chromatography. The former process is a separatory method wherein fluid components with differing net charges are distinguished and isolated by means of elution (stepwise or with a continuously applied gradient) with eluents of differing ionic strength. A gel matrix (resin) carrying either a positive or negative charge is employed to adsorb (bind) components of opposing net charge. During desorption (elution) charged sample components are exchanged by salt ions in the selected eluent, with specific sample components eluting at specific ionic strengths. Reverse phase adsorption chromatography involves separation of fluid sample components based on differing polarity. Sample components are adsorbed to a granulated gel matrix (resin) by non-covalent bonds. Thereafter, stepwise or continuous gradient elution results in, selective desorption of components upon exchange with a non-polar solvent in the eluent.

While the numerous separatory techniques mentioned above are routinely employed in the separation of relatively small hydrophobic and hydrophilic molecules, they have somewhat limited applicability in preparative separations of relatively large molecules such as proteins, especially complex proteins such as lipoproteins, nucleoproteins and glycoproteins. Illustrative of the state of the art in protein separations are reviews by Brown, et al., *Analytical Biochemistry*, 99, 1-21 (1979) and Rubinstein, *Analytical Biochemistry*, 99, 1-7 (1979). See also, "VYDAC TM Comprehensive Guide to Reverse Phase Materials for HPLC", The Sep/A/Ra/-Tions Groups, Hesperia, Calif. and the publication of co-applicants Strickland and co-workers in Parsons, et al., *Endocrinology*, 114, (6), 2223-2227 (1984). Further, to the extent that, for example, reverse phase HPLC procedures have been suggested or employed in isolations of proteins or polypeptides, non-polar solvents generally recommended have included reagents that are difficult to handle or to separate from the desired protein such as acetonitrile. See Parsons, et al., supra. Only a single reference is known to exist disclosing elution with ethanol, specifically aqueous ethanol/formic acid mixtures. See Takagaki, et al. *Journal of Biological Chemistry*, 5, (4), 1536-1541 (1980).

The apparent limited utility of the abovenoted techniques in preparatory separations of high molecular weight complex proteins is especially problematic in view of recent intensive efforts directed toward isolation, purification and application to therapeutic, immunoprophylactic and diagnostic procedures of a wide variety of complex viral and eucaryotic proteins available in only minute quantities from natural sources wherein they are found in association with myriad other complex proteins. As one example, biochemically significant mammalian hematopoietic factors such as erythropoietin, thrombopoietin, granulopoietin and granulocytemarcophage colony stimulating factor are available in extremely small quantities from urine of aplastic anemia patients. Recovery procedures from urinary fluid sources have generally been very complex, costly and labor-intensive and have generated relatively low yields of active product. A widely practiced method for obtaining biologically active preparations of urinary erythropoietin (a high molecular weight, high sialic acid content glycoprotein) may be found in Miyake, et al., *Journal of Biological Chemistry*, 252 (15), 5558-5564 (1979). The seven-step procedure includes ion exchange chromatography, ethanol precipitation, gel filtration, and adsorption chromatography and is reported to provide a 21% yield of glycoprotein with 70,400 Units/mg potency.

The extensive application of recombinant methodologies to the large scale preparation of eucaryotic proteins has substantially enhanced the prospects for obtaining the desired molecules in quantity and in some instances even simplified purification procedures needed to obtain biologically active materials. Illustratively, where the desired recombinant proteins need not be glycosylated to possess biological activity, large quantities of protein can often be produced in E.coli recombinant hosts in the form of insoluble "inclusion bodies" which contain few proteinaceous contaminants, proteases, or the like. Where glycosylation and/or host membrane processing to develop proper secondary and tertiary conformation are required for biological activity, however, eucaryotic hosts such as yeast and mammalian cells in culture (e.g., COS-1 and CHO cells) provide more suitable recombinant hosts. Use of such hosts, however, generally gives rise to increased difficulty in recovery of biologically active forms of proteins in good yield. Host cell lysates frequently include proteinaceous constituents of sufficiently similar molecular weight, charge, polarity and solubility characteristics (vis-a-vis the recombinant protein) to make ready separation difficult. Further proteolytic enzymes endogenous to the host provide a relatively chronic source of biological activity loss for the desired protein. Where recombinant products are secreted into media supernatants by the host cells, similar problems attend isolation from, e.g., culture media from growth of transformed mammalian cell cultures owing principally to the complexity of the media employed.

There thus continues to exist a need in the art for rapid and efficient preparative separatory procedures suitable for recovery of biologically active proteins from fluid sources and most especially for recovery of complex recombinant proteins such as recombinant erythropoietin from variously "contaminated" fluids such as mammalian cell culture supernatants.

The disclosures of co-owned, co-pending U.S. patent application Ser. No. 675,298, entitled "Production of Erythropoietin", filed Nov. 30, 1984, by FuKuen Lin (corresponding to PCT No. US84/02021, filed Dec. 11, 1984, scheduled for publication June 20, 1985 as No.

WO85/02610) are specifically incorporated by reference herein for the purpose of relating the background of the present invention, especially with respect to the state of the art regarding recombinant methodologies applied to large scale production of mammalian erythropoietin.

BRIEF SUMMARY

The present invention provides novel chromatographic separatory procedures individually and jointly suitable for use in the isolation of proteins and specifically applicable to the isolation of erythropoietin, especially recombinant erythropoietin, in biologically active form from fluids, especially mammalian host cell culture supernatants.

According to one of its aspects, the present invention provides for the rapid and efficient recovery of erythropoietin from a fluid by means of a reverse phase liquid chromatographic separation involving selective binding of the desired compound to a $C_4$ or $C_6$ resin followed by elution with aqueous ethanol in about 50 to 80 percent solution at a pH of from about 4.5 to 8.0. In a highly preferred mode of practice of this aspect of the invention, high yields of biologically active recombinant erythropoietin are recovered from mammalian host cell culture supernatants through use of a $C_4$ resin and elution at pH 7.0 employing, stepwise or with a continuous gradient, an eluent comprising about 60 percent aqueous ethanol. Culture supernatants are preferably concentrated before chromatographic treatment and suitable steps are taken to remove ethanol from collected eluent fractions containing erythropoietin. The above elegantly simply separatory procedure reproducibly allows for isolation of erythropoietin having high specific activity in yields approaching 50 percent or more.

In another of its aspects, the present invention provides for rapid and efficient recovery of erythropoietin from a fluid by means of anion exchange chromatography involving selective binding of erythropoietin to a selected cationic resin, treatment of bound materials to guard against acid activation of proteases present, selective elution of bound materials having pKa's greater than that of erythropoietin with aqueous acid at pH's of from about 4.0 to about 6.0, and then elution with aqueous salt at about pH 7.0. Erythropoietin-containing eluent fractions are enriched with biologically active material but may optionally be subject to further processing, e.g., by gel filtration upon ethanol removal. In a presently highly preferred mode of practice of this aspect of the invention, high yields of biologically active recombinant erythropoietin are recovered from mammalian host cell culture supernatants through anion exchange chromatography employing a DEAE agarose resin. Following loading of the DEAE column, urea is added to protect against subsequent acid activation of proteases present and bound fluid components having pKa's greater than erythropoietin are eluted by washings with aqueous acid at about pH 4.3. Thereafter, the pH is adjusted to about 7.0 and aqueous salt is applied stepwise or in a continuous gradient to selectively elute biologically active erythropoietin.

In still another of its aspects, the invention provides for an erythropoietin recovery procedure involving serial application of the ion exchange and reverse phase liquid chromatographic procedures previously described. More specifically, erythropoietin (especially recombinant erythropoietin) is recovered from a fluid (such as a mammalian host cell culture supernatant) in the following stepwise manner. Culture supernatant pools (preferably preliminarily diafiltered and concentrated) are loaded on an anionic exchange column at about pH 7.0 and erythropoietin selectively binds to the cationic resin (preferably DEAE agarose). Bound materials are stabilized against acid activated protease degradation (preferably by addition of urea) and bound materials having pKa's greater than erythropoietin are eluted by one or more aqueous acid washed at from about pH 4.0 to pH 6.0 (preferably about pH 4.3). Thereafter, biologically active erythropoietin is eluted with aqueous salt at about pH 7.0. The erythropoietin-containing eluent fractions are than subjected to reverse phase liquid chromatography on a $C_6$ or, preferably, $C_4$ resin to selectively bind erythropoietin. Bound biologically active erythropoietin is then eluted at from about pH 4.5 to about pH 8.0 (preferably about pH 7.0) with an aqueous ethanol solution of from about 50 to 80 (preferably about 60) percent. The desired erythropoietin is isolated within erythropoietin-containing eluent fractions (as determined by absorbance at 280 nm. Ethanol may then be removed and the product may be subjected to gel filtration (e.g., using a Sephacryl S-200 column) with development using, e.g., a pharmaceutical formulation buffer such as 20 mm sodium citrate/100 mm sodium chloride, pH 6.8 to 7.0.

Other aspects and advantages of the present invention will be apparent upon consideration of the following detailed description of the practice of preferred embodiments thereof.

DETAILED DESCRIPTION

Practice of the present invention is believed to be suitably illustrated by the following examples practiced on pooled CHO cell supernatants prepared in the manner described in Example 10 of the aforementioned U.S. patent application Ser. No. 675,298. More specifically, the treated supernatants were derived from cell strain CHO pDSVL-gHuEPO "amplified" by means of MTX and grown in roller bottles in serum-free medium as described at page 62 of the application. Example 1 generally refers to recovery of biologically active recombinant human erythropoietin by means of a reverse phase liquid chromatography. Example 2 relates to a composite recovery procedure practiced on the same supernatant material. Example 3 relates to RIA and in vivo assays performed on the resulting purified materials.

EXAMPLE 1

Unconcentrated culture supernatant obtained by pooling first and second (7-day) cycle supernatants was loaded on a closed (high pressure configuration) column laboratory packed with $C_4$ matrix (VYDAC TM 214TP-B). A 0.45×10 mm column was employed with a flowrate of 1 ml/min. Following sample application, biologically active recombinant erythropoietin was eluted with a linear gradient from 10 mm Tris, pH 7.0 to 80% EtOH/10 mm Tris, pH 7.0. Protein concentration was UV monitored at 230 nm and the fractions of eluent at about 60% EtOH were pooled.

EXAMPLE 2

The composite recovery procedure of this example consisted of serial practice of ion exchange and reverse phase chromatographic procedures performed on a larger fraction of supernatant than in Example 1. The chromatographic procedures were preceded by concentration and diafiltration steps and followed by a gel filtration processing step.

1. Concentration and Diafiltration

First and second (7-day) growth cycle supernatants were separately concentrated thirty-fold using a Pellicon ultrafiltration device (Millipore, Bedford, Mass.) with a 10,000 MW cutoff. Concentrated first and second cycle media were pooled and diafiltered on the Pellicon device against 10 mm Tris at about pH 7.0. Pellicon device against 10 mm Tris at about pH 7.0. (The diafiltered media may optionally be made 20 μm in $CuSo_4$ before ion exchange chromatography.) It may be noted that any ultrafiltration device with a 10,000 or 30,000 MW cutoff may be used and that the diafiltration step may be performed against any suitable low ionic strength buffer at a pH of from about 6.0 to 8.5.

2. Ion Exchange Chromatography

The concentrated, diafiltered media from step 1 was pumped on a relatively low density DEAE agarose column (Bio-Rad, Richmond, Calif.). The column was then washed with three volumes of 5 mm acetic acid/1 mm glycine/6 M urea at about pH 4.5. Optionally, the wash may include 20 μm $CuSO_4$ to assist in oxidation of sulfhydryl groups on the desired protein. Glycine was incorporated to react with any cyanate present. Urea serves to stabilize against acid activation of proteases at low pH and to assist in solubilization of proteins. Following the washings which serve to elute off bound materials with greater pKa's than erythropoietin, the column was washed with 25 mm NaCl/10 mm Tris at about pH 7.0 to return to neutral pH and remove urea. Biologically active erythropoietin was eluted with 75 mm NaCl/10 mm Tris at about pH 7.0. $CuSo_4$ (20 μm) can optionally be included in both the neutralizing wash and/or the elution step.

3. Reverse Phase Chromatography

The procedure applied was essentially as in Example 1 except that an open column, low pressure mode was employed. Following identification of the erythropoietin "peak" in gradiant fractions at about 60% ethanol, it is preferred to dilute the collected fraction(s) five-fold with, e.g., 10 mm TRIS at pH 7.0 to reduce ethanol concentration and facilitate ethanol with a small amount of buffer (20 mm sodium citrate/100 mm sodium chloride.

4. Gel Filtration

Products of step 3 from which ethanol has been removed was loaded on a column of Sephacryl S-200 (Pharmacia, Piscataway, N.J.). The column was developed using a projected pharmaceutical formulation buffer of 20 mm sodium citrate/100 mm sodium chloride at pH 6.8 to 7.0.

EXAMPLE 3

Radioimmunoassay and in vivo bioassay procedures as described in the above-mentioned U.S. patent application Ser. No. 675,298 were performed using the recombinant erythropoietin recovered by the procedures of Example 1 and 2. The experimental data indicated yields of 52 and 16 percent, respectively, for the Example 1 and 2 products, with ratios of in vivo to RIA activity of 1.02 and 1.3. Subsequent repeats of the Example 2 procedure on different supernatants have provided yields on the order of 48-50 percent.

While the foregoing illustrative examples have described procedures of the invention as practiced for recovery of erythropoietin from mammalian cell culture sources, the procedures are believed to be suitable for recoveries practiced on other culture fluids such as mammalian lysate/supernatant combination and similar fluids derived from yeast cell cultures. Similarly, the individual and composite procedures (and especially the ion exchange chromatographic procedures) are expected to be useful in recovery of erythropoietin from natural sources such as urine.

It will be apparent to those skilled in the art that the procedures above applied to recovery of erythropoietin can be expected to find applicability in recovery of other complex proteins, especially glycoproteins produced by recombinant methodologies. Glycoproteins whose recovery is within the contemplation of the invention include such distinct products as recombinant tissue plasminogen activator, Factor VIII and Herpes Simplex Virus Glycoprotein D.

What is claimed is:

1. A process for the efficient recovery of erythropoietin from a fluid, said process comprising the following steps in sequence:
    subjecting the fluid to ion exchange chromatographic separation at about pH 7.0, thereby to selectively bind erythropoietin in said sample to a cationic resin;
    stabilizing materials bound to said resin against degradation by acid activated proteases;
    selectively eluting bound contaminant materials having a pKa greater than that of erythropoietin by treatment with aqueous acid at a pH of from about 4.0 to 6.0; and
    selectively eluting erythropoietin by treatment with an aqueous salt at a pH of about 7.0; and
    isolating erythropoietin-containing eluent fractions.

2. The process of claim 1 applied to recovery of recombinant erythropoietin from a cell culture derived fluid.

3. The process of claim 2 applied to recovery of erythropoietin from a mammalian cell culture derived fluid.

4. The process of claim 3 applied to recovery of erythropoietin from a mammalian cell culture supernatant.

5. The process of claim 1 applied to recovery of erythropoietin from urinary fluids.

6. The process of claim 1 wherein the cationic resin is a DEAE agarose resin.

7. The process of claim 1 wherein said stabilizing step comprises treatment with urea.

8. A process for the efficient recovery of erythropoietin from a fluid, said process comprising the following steps in sequence:
    (1) subjecting the fluid to ion exchange chromatographic separation at about pH 7.0, thereby to selectively bind erythropoietin in said sample to a cationic resin;
    (2) stabilizing materials bound to said resin against degradation by acid activated proteases;
    (3) selectively eluting bound contaminant materials having a pKa greater than that of erythropoietin by treatment with aqueous acid at a pH of from about 4.0 to 6.0;
    (4) selectively eluting erythropoietin by treatment with an aqueous salt at a pH of about 7.0;

(5) subjecting eluted, erythropoietin-containing fluids to reverse phase liquid chromatographic separation involving an immobilized $C_4$ or $C_6$ resin, thereby to selectively bind erythropoietin in said fluid to said resin;

(6) selectively eluting bound erythropoietin from said resin with an aqueous ethanol solution of from 50 to 80 percent at a pH of from about 4.5 to about 8.0; and, (7) isolating erythropoietin-containing fractions of the eluent.

9. The process of claim 8 applied to recovery of recombinant erythropoietin from a cell culture derived fluid.

10. A process for the efficient recovery of recombinant erythropoietin from a mammalian cell culture supernatant fluid, said process comprising the following steps in sequence:

(1) subjecting the fluid to ion exchange chromatographic separation at about pH 7.0, thereby to selectively bind erythropoietin in said sample to a DEAE agarose cationic resin;

(2) stabilizing materials bound to said resin against degradation by acid activated proteases through treatment with urea;

(3) selectively eluting bound materials having a pKa greater than that of erythropoietin by treatment with aqueous acid at a pH of about 4.3.

(4) selectively eluting erythropoietin by treatment with an aqueous salt at a pH of about 7.0;

(5) subjecting erythropoietin-containing eluent fractions to reverse phase liquid chromatographic separation involving an immobilized $C_4$ resin, thereby to selectively bind erythropoietin in said fluid to said resin;

(6) selectively eluting bound erythropoietin from said resin with an aqueous ethanol solution of about 60 percent at a pH of about 7.0; and, (7) isolating erythropoietin-containing fractions of the eluent.

11. The process of claim 10 further including the step of removal of ethanol from isolated erythropoietin-containing fractions.

* * * * *